US006387238B1

(12) United States Patent
Merk et al.

(10) Patent No.: US 6,387,238 B1
(45) Date of Patent: May 14, 2002

(54) ELECTROLYTIC SYNTHESIS OF PERACETIC ACID

(75) Inventors: Tom L. Merk, Chesterland; Paul S. Malchesky, Painesville Township; Chung-Chiun Liu, Cleveland Hts., all of OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/630,934

(22) Filed: Aug. 2, 2000

Related U.S. Application Data
(60) Provisional application No. 60/147,327, filed on Aug. 9, 1999.

(51) Int. Cl.[7] .............................. C25B 3/00; C25B 9/00; C25C 7/00
(52) U.S. Cl. .................... 205/439; 205/440; 204/275.1; 204/252
(58) Field of Search .............................. 204/194, 275.1, 204/252; 205/439, 440

(56) References Cited

U.S. PATENT DOCUMENTS

| | | | |
|---|---|---|---|
| 3,884,777 A | 5/1975 | Harke et al. .................. | 204/84 |
| 4,142,949 A | 3/1979 | Faul et al. ..................... | 204/84 |

(List continued on next page.)

FOREIGN PATENT DOCUMENTS

| | | |
|---|---|---|
| CA | 02214957 | 11/1997 |
| EP | 0 244 565 A1 | 2/1987 |
| EP | 0 395 296 | 10/1990 |
| JP | 05302287 | 11/1993 |
| WO | WO 93/18854 | 3/1993 |
| WO | WO 99/08719 | 2/1999 |
| WO | WO 99/39753 | 8/1999 |

OTHER PUBLICATIONS

Khomutov, et al. ("Study of the Kinetics of Anodic Processes in Potassium Acetate," *Izv. Vyssh. Uchebn. Zaved., Kim. Teknol.* 31(11) pp. 71–74 (1988) no month available.

*Primary Examiner*—Edna Wong
(74) *Attorney, Agent, or Firm*—Fay, Sharpe, Fagan, Minnich & McKee, LLP

(57) ABSTRACT

An electrolysis unit (10, 210, 310) has an anode (16, 216,316) and a gas diffusion cathode (18, 218, 318). Air is fed to the cathode (18, 218) to generate peroxide species, such as hydrogen peroxide, peroxide ions, or peroxide radicals by electrolysis of oxygenated water. A peracetic acid precursor, such as acetyl salicylic acid, reacts with the peroxide to form peracetic acid. An ion selective barrier (20, 220) optionally separates the unit into two chambers, an anodic chamber (12, 212) and a cathodic chamber (14, 214). By selecting either a proton permeable membrane or an anion exchange membrane for the barrier, the peracetic acid may be formed in either an alkaline electrolyte in the cathodic chamber or in an acid electrolyte in the anode chamber, respectively.

28 Claims, 6 Drawing Sheets

U.S. PATENT DOCUMENTS

| | | | |
|---|---|---|---|
| 4,350,575 A | 9/1982 | Porta et al. | 204/84 |
| 4,357,217 A | 11/1982 | Kuehn et al. | 204/84 |
| 4,384,931 A | 5/1983 | Jasinski et al. | 204/84 |
| 4,430,176 A | 2/1984 | Davison | 204/84 |
| 4,440,611 A | 4/1984 | Dhar et al. | 204/147 |
| 4,455,203 A | 6/1984 | Stucki | 204/84 |
| 4,487,669 A | 12/1984 | Kuwana | 204/101 |
| 4,560,455 A | 12/1985 | Porta et al. | 204/130 |
| 4,693,794 A | 9/1987 | Chiang | 204/84 |
| 4,731,173 A | 3/1988 | Chiang | 204/265 |
| 4,753,718 A | 6/1988 | Chiang | 204/265 |
| 4,758,317 A | 7/1988 | Chiang | 204/84 |
| 4,836,859 A | 6/1989 | Konishi et al. | 134/1 |
| 4,872,957 A | 10/1989 | Dong et al. | 204/84 |
| 4,909,911 A | 3/1990 | Bear et al. | 204/84 |
| 4,927,509 A | 5/1990 | Mathur et al. | 204/83 |
| 5,302,345 A | 4/1994 | Oksman et al. | 422/30 |
| 5,316,629 A | 5/1994 | Clifford et al. | 204/83 |
| 5,316,740 A | 5/1994 | Baker et al. | 422/186.07 |
| 5,358,609 A | 10/1994 | Drackett | 204/84 |
| 5,385,711 A | 1/1995 | Baker et al. | 422/186.07 |
| 5,437,771 A | 8/1995 | Shimamune et al. | 204/84 |
| 5,611,088 A | 3/1997 | Almon | 4/222 |
| 5,643,437 A | 7/1997 | Dong et al. | 205/348 |
| 5,645,700 A | 7/1997 | White et al. | 204/252 |
| 5,770,033 A | 6/1998 | Murphy et al. | 205/464 |

ELECTROLYTIC SYNTHESIS OF PERACETIC ACID

This application claims the benefit of U.S. Provisional Application Serial No. 60/147,327; filed Aug. 5, 1999.

BACKGROUND OF THE INVENTION

The present invention relates to the sterilization and disinfection arts. It finds particular application in conjunction with electrochemically produced solutions containing oxidizing agents, such as peracetic acid, for sterilization or disinfection of medical and pharmaceutical equipment, food products, and the like, and will be described with particular reference thereto. It should be appreciated, however, that the invention is also applicable to other sterilization, disinfection, and sanitization methods, including treatment of water, food service equipment, and the like and has applications in bleaching and in chemical synthesis.

Peracetic acid is a useful disinfectant or sterilant for a variety of applications. Peracetic acid has a number of uses, including disinfection of waste and sterilization of medical equipment, packaging containers, food processing equipment, and the like. It poses few disposal problems because it decomposes to compounds (i.e., acetic acid and oxygen) which are readily degraded in sewage treatment plants or by soil bacteria. It has a broad spectrum of activity against microorganisms, and is effective even at low temperatures.

Conventionally, peracetic acid concentrations are produced from solutions of acetic acid and hydrogen peroxide at acidic pH. The concentrated solutions are mixed with water and other chemicals to form a dilute solution. Items to be decontaminated, either by sterilization or disinfection, are then immersed in the solution for a sufficient period to effect the required level of decontamination. The decontaminated items are then typically rinsed before use. To ensure effective sterilization or disinfection within a preselected period of time, the concentration of peracetic acid is preferably at or above a minimum effective level, typically around 1000–2000 ppm for sterilization of medical instruments. When the peracetic acid concentration is at or above the minimum effective level for sterilization, sterilization is expected in the time period for contact. Lower levels of peracetic acid are effective as disinfectants. Concentrations as low as 2–10 ppm, or less, have been shown to be effective for disinfection, which requires only the destruction of pathogenic microorganisms.

While single use formulations of peracetic acid are available, in facilities where items are being sterilized or disinfected at frequent intervals throughout the day, the same batch of peracetic acid solution is often used repeatedly. However, peracetic acid tends to decompose over time. For example, a disinfectant solution, which is above the minimum effective peracetic acid concentration for sterilization at the beginning of a day, frequently drops below the effective concentration without further additions of the concentrated peracetic acid or precursors. Elevated ambient temperatures, the quantity of items sterilized or disinfected, and the degree of contamination of the items, all contribute to reducing the useful life of the batch. In addition, storage conditions sometimes lead to degradation of the peracetic acid precursors before use.

Moreover, the concentrated peracetic acid or precursors tend to be hazardous materials which sometimes pose shipment and storage problems. Because of the risks of storage and also the fact that they degrade over time, it is preferable to maintain a limited supply of the concentrate or precursors and reorder them at frequent intervals.

Recently, the cleaning and decontamination properties of solutions formed by the electrolysis of water under special conditions have been explored. Electrolysis devices are known which receive a supply of water, such as tap water, commonly doped with a salt, and perform electrolysis on the water. During electrolysis, an anolyte solution is produced from the doped water at an anode and a catholyte solution is produced at a cathode. Examples of such water electrolysis units are as described in U.S. Pat. Nos. 5,635,040; 5,628,888; 5,427,667; 5,334,383; 5,507,932; 5,560,816; and 5,622,848.

To create these anolyte and catholyte solutions, tap water, often with an added electrically or ionically conducting agent, is passed through an electrolysis unit or module. The unit has an anodic chamber and a cathodic chamber, generally separated from each other by a partially-permeable barrier. Conducting agents are often halogen salts, including the salts sodium chloride and potassium chloride. An anode and a cathode contact the water flowing in the respective anodic and cathodic chambers. The anode and cathode are connected to a source of electrical potential to expose the water to an electrical field. The barrier may allow the transfer of selected electron carrying species between the anode and the cathode but limits fluid movement between the anodic and cathodic chambers. The salt and minerals naturally present in and/or added to the water undergo oxidation in the anodic chamber and reduction in the cathodic chamber.

An anolyte resulting at the anode and a catholyte resulting at the cathode can be withdrawn from the electrolysis unit. The anolyte and catholyte may be used individually or as a combination. The anolyte has been found to have anti-microbial properties, including anti-viral properties. The catholyte has been found to have cleaning properties.

However, electrochemically activated water is not without shortcomings. Electrochemically activated water has a high surface energy, which does not readily allow for penetration of the electrochemically activated water into creviced areas of medical instruments. Thus, complete kill may not be achieved. Further problems have arisen on metal surfaces coming into contact with the electrochemically activated water, including the surfaces of the decontamination equipment and metal medical devices. The electrochemically activated water is corrosive to certain metals. Stainless steel, used to produce many medical devices, is particularly susceptible to corrosion by electrochemically activated water.

Other chemicals are also amenable to electrochemical conversion. Khomutov, et al. ("Study of the Kinetics of Anodic Processes in Potassium Acetate," *Izv. Vyssh. Uchebn. Zaved., Khim. Teknol.* 31(11) pp. 71–74 (1988)) discloses a study of the conversion of acetate solutions to peracetic acid and acetyl peroxide in the temperature range of −10° C. to 20° C. using a three-electrode cell. The anode and cathode regions of the cell were separated by a barrier of porous glass. Anodes of platinum, gold or carbon, at a high potential, typically 2–3.2 V relative to a silver/silver chloride reference electrode, were used in the study. Potassium acetate concentrations were initially 2–10 mol/L. From conductivity and viscosity measurements, Khomutov, et al. estimated that peracetic acid solutions were generated at the anode with concentrations of active oxygen of 0.1 gram equivalents/L. However, no direct measurements of peracetic acid concentration in the bulk solution were made.

Moreover, the pH range of 8.2–10.4 disclosed by Khomutov, et al. is undesirable for many practical decontamination solutions. To reduce corrosion of the metal components of the instruments to be decontaminated, a pH of close to neutral is desirable.

The present invention provides a new and improved system and method for generation of peracetic acid and other oxidizing agents which overcomes the above-referenced problems and others.

SUMMARY OF THE INVENTION

In accordance with one aspect of the present invention, a method for preparing an antimicrobial solution containing peracetic acid is provided. The method includes electrolytically generating hydrogen peroxide or peroxide ions or radicals and reacting such species with an acetyl donor to form peracetic acid.

In accordance with another aspect of the present invention, a method of antimicrobial decontamination of items is provided. The method includes supplying an oxygen containing gas to a cathode of an electrolysis unit and forming peroxide species, such as peroxide ions, peroxide radicals, or hydrogen peroxide, in an electrolyte at the cathode. The method further includes reacting the peroxide species with a peracetic acid precursor to form peracetic acid and transporting the electrolyte containing peracetic acid to a site at which the items are microbially decontaminated.

In accordance with another aspect of the present invention, a system for antimicrobial decontamination of items is provided. The system includes an electrolysis unit including an anode and a cathode. A source of an electrical potential applies a potential between the anode and the cathode. A source of an oxygen containing gas supplies oxygen to the cathode for forming peroxide species in an electrolyte. A source of a peracetic acid precursor supplies a peracetic acid precursor for reacting with the peroxide species to form a solution which includes peracetic acid. A vessel receives items to be decontaminated and a fluid supply line carries the solution containing peracetic acid from the electrolysis unit to the vessel.

One advantage of the present invention is that it enables peracetic acid solutions to be prepared in situ, as required, or stored in small batches, until needed.

Another advantage of the present invention is that it enables antimicrobial solutions to be provided on line or in batch form, on demand.

Yet another advantage of the present invention is that the peracetic acid concentration of a solution can be revived or increased by returning the solution to an electrolysis unit.

A further advantage of the present invention is that storage and shipment of concentrated and hazardous sterilants or precursors may be avoided.

A yet further advantage of the present invention arising from the generation of peracetic acid on demand is that decomposition of peracetic acid during shipment and storage is avoided.

Another advantage of the present invention is that it enables the concentration of peracetic acid in a microbial decontamination system to be maintained during repeated use of the system.

Yet another advantage of the present invention is that concentrations of peracetic acid in the range of about 1000 to 2000 ppm can be prepared for sterilization or other applications without employing high concentrations of precursors.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Peracetic acid is manufactured in situ, as needed, for a variety of applications, including decontamination of medical devices and treatment of food products. In a preferred embodiment, hydrogen peroxide is generated in an electrolysis unit by reduction of oxygen in water and then reacted with an acetyl donor, such as acetyl salicylic acid, to form peracetic acid.

Figure 1:
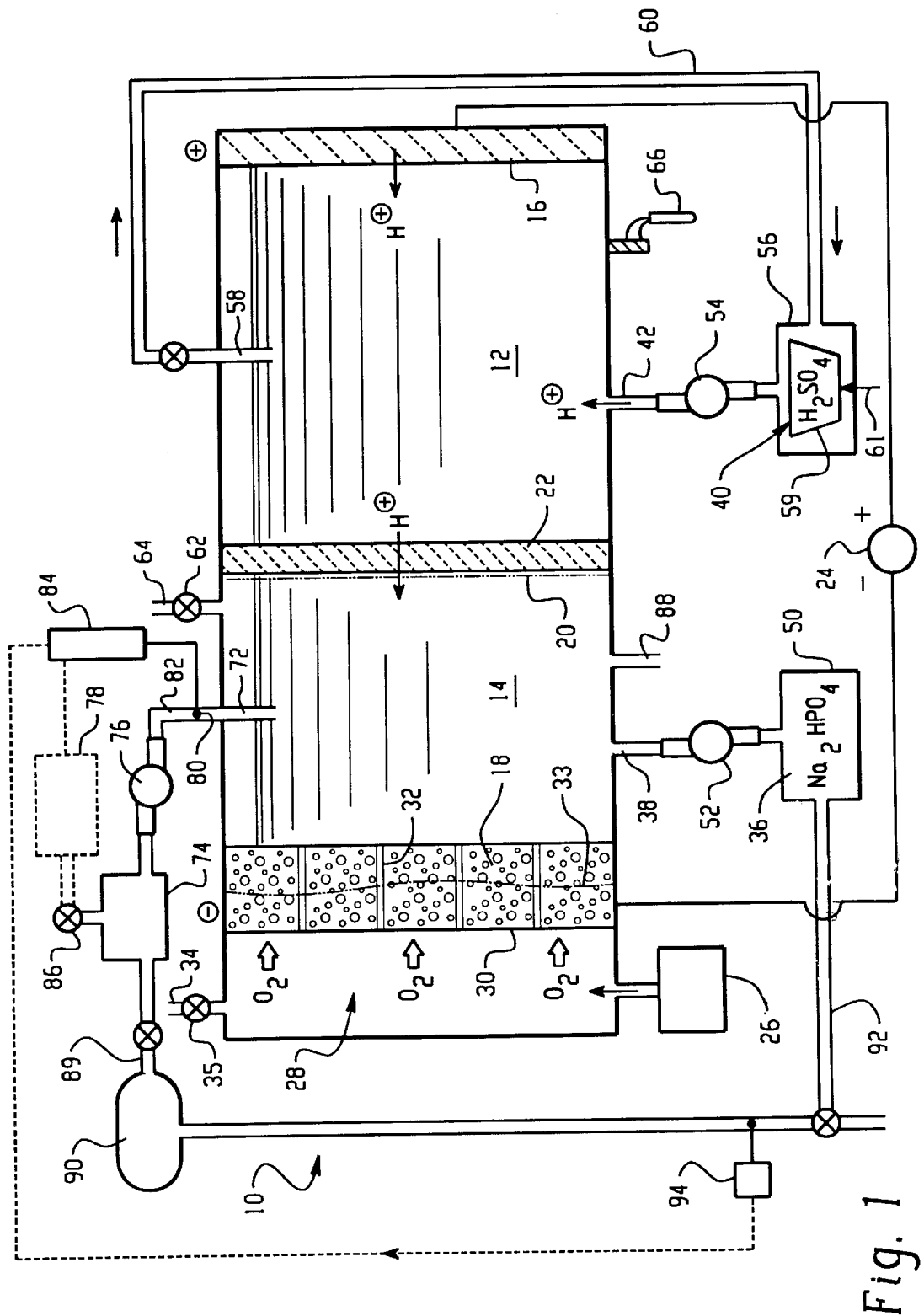
FIG. 1 is a schematic diagram of a preferred embodiment of an electrolysis unit for generation of sterilizing and disinfecting solutions according to the present invention.

With reference to FIG. 1, an electrolysis unit or cell 10 generates oxidizing species for use as liquid sterilants and disinfectants, such as peracetic acid and/or hydrogen peroxide and related shorter-lived oxidizing species. The unit 10 includes two electrode chambers, namely an anodic chamber 12 and a cathodic chamber 14. An electrode is disposed in each of the chambers. Specifically, an anode 16 forms a wall of the anodic chamber and a cathode 18 forms a wall of the cathodic chamber. Other walls of the two chambers may be formed from materials which are compatible with peracetic acid, such as insulated steel, plexiglass, or other suitable material. Preferably, an ion selective barrier or membrane 20 separates the anodic and cathodic chambers 12, 14 and controls the flow of dissolved species between them. In the embodiment of FIG. 1, the barrier 20 is a cation exchange membrane, which permits the migration of protons ($H^+$ ions) between the two chambers, but limits migration of anions between the two chambers. The membrane also acts as a separation or barrier between electrolytes in the two chambers. Particularly preferred cation exchange membranes are sulfonic acid based membranes. Two such proton permeable membranes, NAFIONυ 117 and NAFION™ 450, are available from DuPont and Aldrich. Alternatively, filter paper, such as Fisher brand P-5 filter paper, is used for the membrane 20.

Optionally, the membrane is supported on a liquid permeable support wall 22, such as a wall of porous ceramic.

The support wall provides a physical support for the membrane and permits the movement of liquids and ions to and from the membrane.

Figure 2:
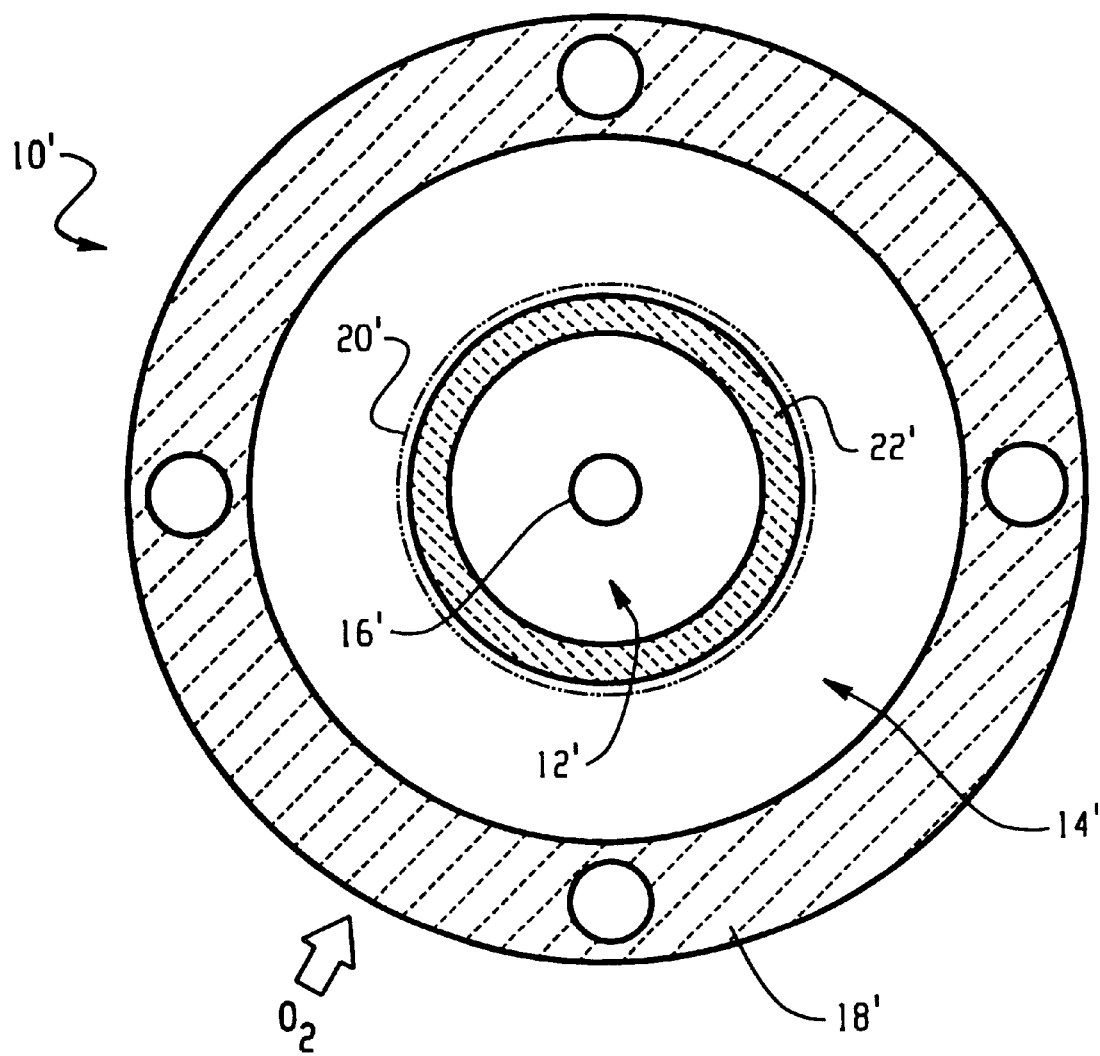
FIG. 2 is a first alternative embodiment of an electrolysis unit according to the present invention.

As will readily be appreciated, the cell 10 may be formed in a variety of configurations. For example, the cell 10' is optionally cylindrical, with the membrane 20' and support wall 22' forming a concentric cylinder, which separates the anodic chamber 12' from the cathodic chamber 14', as shown in FIG. 2 (where like parts are identified with a prime (')). The anode 16' is in the form of a rod which is positioned in the center of the anodic chamber. The cathode 18' forms an exterior wall of the unit.

With reference once more to FIG. 1, a source of electric potential 24 applies a negative potential to the cathode. The applied potential is selected to be high enough for the reduction of oxygen at the cathode. A potential of around 3–30 volts, more preferably, 10–30 volts, relative to Ag/AgCl in 3M NaCl, is preferred for this purpose, with a particularly preferred potential of around 5V. Current densities of from $1 \mu A/cm^2$ to about $1 A/cm^2$ are suitable. In one embodiment, the potential is sufficient to provide a current flow of about 5 amps through a cathode of 50 cm$^2$ in area (100 mA/cm$^2$).

The cathode chamber 14 is fed with a supply of oxygen, or an oxygen containing gas, such as air. Air is an effective source of oxygen for the present application. Preferably, as shown in FIG. 1, the cathode 18 is a gas diffusion electrode which permits the flow of air or other oxygen containing gas therethrough. A compressor 26 supplies air under a slight positive pressure to an air chamber 28 adjacent an exterior surface 30 of the gas diffusion electrode 18. The air passes through pores 32 (shown schematically) in the gas diffusion cathode 18 to an air-liquid-solid interface 33 between the air and the liquid entering the cathode from the cathode chamber.

Excess air is released from the air chamber 28 through an air outlet 34. The outlet preferably includes a regulator valve 35 which controls the outflow of air through the air outlet. This allows the pressure of the air in the air chamber to be adjusted to a suitable level for maintaining an air:liquid:solid interface within the body of the cathode 18.

An "alkaline" electrolyte 36 is supplied to the cathode chamber 14 through an inlet 38. The electrolyte carries charge through the cathode chamber. An "acidic" electrolyte 40, is fed to the anode chamber through an inlet 42. While the two electrolytes 36, 40 will be described herein as "alkaline" and "acidic," it is to be understood that these terms are used relatively, to indicate a pH differential between the two electrolytes. The pH differential is preferably at least about 0.5, more preferably, about 5 or higher. Thus, the "alkaline" electrolyte may be acid, (i.e., less than pH 7) or the "acid" electrolyte, alkaline (i.e., greater than pH 7). In all cases, however, the alkaline electrolyte in the cathode chamber 14 is always at a higher pH (i.e., is more basic) than the acid electrolyte in the anode chamber 12 and conversely, the acid electrolyte is always at a lower pH (i.e., more acidic) than the alkaline electrolyte. In the embodiment of FIG. 1, the alkaline electrolyte preferably has a pH of about 5–14, more preferably, a pH of 7–9, and most preferably 7–7.5, while the acid electrolyte preferably has a pH of from 0 to about 4, more preferably 0–3, the difference between the alkaline and acid pH preferably providing a pH gradient of about 5–7, or more. The acidic electrolyte is thus one which is of sufficient strength to maintain a pH gradient across the membrane. A sulphuric acid solution at a concentration of about 5% is a suitable acidic electrolyte and has a pH of about 0.2.

The alkaline electrolyte includes a solution of electrolyte ions in water. The ions carry charge through the electrolyte. Suitable charge carrying ions are provided by salts of alkali and alkaline earth metals, such as phosphates, carbonates, silicates (such as zeolites), and sulfates of sodium and potassium, or other electrolyte materials. Bases, particularly, hydroxides, such as sodium hydroxide or potassium hydroxide, may also be used. Phosphates and silicates are particularly preferred electrolytes as these also provide buffering.

A buffering agent is preferably added (where not already present as the charge carrying ion) to the alkaline electrolyte to maintain the alkaline electrolyte at an appropriate pH for generating hydrogen peroxide (preferably, about pH 7–9). A combination of buffers and or other compounds may be used to adjust the pH. For example, acids, such as acetic acid or citric acid may be used to adjust the pH of the alkaline solution. The buffering agent/pH adjuster may also provide the ionic conductance of the electrolyte, as discussed above.

As shown in FIG. 1, the alkaline electrolyte is delivered to the cathodic chamber inlet 38 from a reservoir or holding tank 50 by a pump 52, gravity feed, or other convenient delivery system. The buffering agent is preferably combined with other components of the electrolyte in the alkaline electrolyte reservoir 50. Alternatively, it is metered directly into the chamber from a separate reservoir (not shown). Obviously, the pump 52 and reservoir 50 could be eliminated if a batch process was desired.

A second pump 54 circulates the sulphuric acid solution, or other acidic electrolyte, through the anode chamber via the anode chamber inlet from a reservoir 56 of sulphuric acid solution. Peristaltic pumps are suitable pumps 52, 54.

The sulphuric acid is essentially unconsumed in the electrolysis process of the embodiment of FIG. 1. It is preferably circulated continuously through the anode chamber. Specifically, the acid electrolyte is withdrawn from the anode chamber through an outlet 58, transported to the reservoir 56 through a return line 60, and then returned to the chamber 12. In this way, a constant flow of the acid electrolyte over the anode is maintained.

Alternatively, the acid electrolyte solution is not circulated into and out of the anode chamber 12 during the electrolysis, but remains in the anode chamber. Optionally, it is stirred in the anode chamber to maintain a flow of electrolyte over the anode. The acid electrolyte 40 may be reused for extended periods of continuous peracetic acid generation or for the production of several batches of peracetic acid. Optionally, the acid electrolyte is introduced into the anode chamber 12 or the acid electrolyte reservoir 56 in the form of a sealed ampule 59, such as a plastic cup. The cup is opened by an opener member 61 in the reservoir when a lid to the reservoir is closed. Optionally, water is added to the reservoir to dilute a concentration acid solution to form the acid electrolyte.

Optionally, an air outlet 62 for the cathode chamber allows air which has bubbled through the electrolyte to leave the chamber. The air outlet may include a check valve or pressure relief valve 64, which opens when the chamber pressure reaches a preselected minimum pressure.

The oxygen is converted at the cathode 18 to peroxide ions, generally as follows:

$$O_2 + 2H_2O \rightarrow 2HO_2^- + 2H^+$$

or $$O_2 + 2OH^- \rightarrow 2HO_2^-$$

or $$O_2 + H_2O + 2e^- \rightarrow HO_2^- + OH^-$$

Free radicals of peroxide may also be formed. The peroxide ions/radicals react with hydrogen ions or water to form hydrogen peroxide.

$$HO_2^- + H^+ \rightarrow H_2O_2$$

or $$HO_2^- + H_2O \rightarrow H_2O_2 + OH^-$$

Protons (H$^+$) generated at the anode 16 are able to pass through the membrane 20 into the cathode chamber 14 to take part in the reaction.

Temperatures of from about freezing to the boiling point of the electrolyte solution, more preferably about 10–60° C., most preferably, about 15–30° C., are suitable for the reactions taking place within the electrolysis unit 10. Accordingly, it is not necessary to heat the anode or cathode chambers. Heat may be generated during the reaction, causing the temperature to rise.

Solutions formed from the electrolyte solutions in the anodic and cathodic chambers 12, 14 during electrolysis are referred to as the anolyte and catholyte, respectively. In the embodiment of FIG. 1, for example, the catholyte comprises a solution of hydrogen peroxide and peroxide ions/radicals (all are referred to herein as "peroxide species") with phosphate buffers. Other oxidizing species may also be present, such as peracetic acid, as will be discussed in greater detail below.

The anode 16 and cathode 18 preferably have large surface areas. The anode is preferably a dimensionally stable anode (DSA). Suitable materials for the anode 16 include, but are not limited to, carbon (including graphite), platinum, iridium oxide, lead dioxide, palladium oxide, and ruthenium oxide. In the case of iridium oxide, lead dioxide, palladium oxide, or ruthenium oxide, the oxide is preferably disposed on a substrate, such as a titanium wire mesh or other noble metal substrate, which supports the oxide and provides the anode with a large surface area. Other suitable anode materials include precious metal-doped carbon or metal, such as precious metal-doped stainless steel, platinum, or palladium. Other materials suitable for forming the anode include silver, molybdenum, platinum, or cobalt on a nickel support material, which is in the form of a film sheet, screen, block, foam, or the like.

The cathode 18 is formed from any suitable electron acceptor, such as platinum, titanium, gold, or carbon (including graphite). Carbon, such as graphite, is particularly preferred for generation of hydrogen peroxide. A suitable gas diffusion electrode 18 includes a substrate, formed from a sheet of a conductive material, such as gold or nickel, which has a mesh structure with fine pores for admitting the oxygen. A layer of carbon, or other electron acceptor, is coated on the substrate. The mesh provides support for the active material (carbon) of the cathode. Cathodes 18 comprising packed carbon beds, carbon frit, or open-celled porous or sintered materials coated with carbon may also be used. Other suitable cathode materials include platinum black, platinum/ruthenium on carbon black, platinum on carbon black, and carbon black.

The pressure of the entering air keeps liquids from passing through the gas diffusion cathode 18 into the air chamber 28. Similarly, the pressure of the liquid within the cathode chamber tends to keep gas from passing through the cathode into the cathode chamber 14. The liquid-gas-solid interface 33 within the cathode is where the oxygen reduction reaction primarily takes place. Some GDEs are provided with a hydrophobic membrane on the oxygen side and thus do not permit liquid passage through the electrode.

Optionally, the anodic chamber is fluidly connected with a reference electrode 66, such as a silver/silver chloride electrode, to ensure that the selected applied potential is being maintained. The reference electrode is preferably positioned as close to the anode as possible to eliminate the effects of solution resistance on the measured potential.

The catholyte contains hydrogen peroxide and peroxide ions/radicals generated in the cathode chamber. A peracetic acid precursor, such as an acetyl donor, is reacted with the peroxide species in the catholyte solution to form peracetic acid. For example, the reaction proceeds as follows:

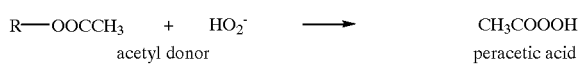

where R may be H, alkyl, aryl, alkali metal, such as Na, K, or the like. The reaction between acetyl salicylic acid and H$_2$O$_2$ (or its precursor species), for example, results in the formation of salicylic acid and peracetic acid. A single molecule of tetraacetyl ethylene diamine (TAED) produces two molecules of peracetic acid in reaction with two molecules of H$_2$O$_2$. The catholyte may also include a variety of other both short lived and/or longer living oxidizing species, which react directly with the peracetic acid precursor or which participate in reaction paths which lead to the formation of peracetic acid from the precursor.

Suitable acetyl donors include, but are not limited to O-acetyl donors (—OC(O)CH$_3$), such as acetyl salicylic acid, sodium acetate, potassium acetate, acetic acid, acetaldehyde, ( and β)-D-glucose pentaacetate, cellulose (mono and tri) acetate, D-mannitol hexaacetate, sucrose octaacetate, and acetic anhydride. N-acetate donors (—N—C(O)CH$_3$) may also be used, such as TAED, N-acetyl glycine, N-acetyl-DL-methionine, 6-acetamidohexanoic acid, N-acetyl-L-cysteine, 4-acetamidophenol, and N-acetyl-L-glutamine.

Acetyl salicylic acid, ( and β)-D-glucose pentaacetate, TAED, acetic anhydride, and sucrose octaacetate are particularly effective acetyl donors in this application. However, acetic anhydride is less favored for some applications because of its toxicity. Cellulose acetates,  & β-D-glucose pentaacetates, and D-mannitol hexaacetate may pose solubility problems in some solutions. The maximum amount of peracetic acid which may be generated is limited, to some extent, by the solubility of the acetyl donor. Thus, highly soluble acetyl donors are preferred when relatively high peracetic acid concentrations (above about 1000 ppm) are desired. A particularly preferred acetyl donor is acetyl salicylic acid.

The peracetic acid precursor may be added before, during, or after formation of peroxide species. In one embodiment, shown in FIG. 1, the peracetic acid precursor is added after formation of hydrogen peroxide and other species. Specifically, the catholyte containing hydrogen peroxide is withdrawn from the cathode chamber 14 through an outlet 72 to a holding chamber 74. A pump 76, connected with the outlet 72 is optionally used to pump the catholyte, or, sufficient pressure is supplied by pump 52 to carry the catholyte out of the chamber.

The peracetic acid precursor may be supplied in solid form or as a solution. In the embodiment of FIG. 1, the peracetic acid precursor is supplied to the holding chamber 74 from a reservoir 78 as a solution of the peracetic acid precursor in water. In one embodiment, hydrogen peroxide is held in the holding tank until peracetic acid is needed, and the acetyl donor is then added.

The preferred concentration of the precursor is dependent on the solubility of the precursor and on the desired concentration of the peracetic acid. In a preferred embodiment, the precursor is metered into the holding tank in a stoichiometric amount, i.e., in a sufficient quantity such that all or substantially all of the precursor combines with the peroxide species. In the case of acetyl salicylic acid as the peracetic acid precursor, the acetyl salicylic acid reacts with the peroxide in a concentration ratio (by weight basis) of from about 5:1 to about 25:1.

Optionally, a sensor 80, positioned within the holding tank 74, or positioned in a fluid line 82 connecting the chamber outlet 72 with the holding tank, or at another suitable location, detects the hydrogen peroxide concentration. The sensor 80 preferably signals a control system 84 which regulates the addition of the peracetic acid precursor by opening and closing a valve 86, or other suitable regulator, between the reservoir 78 and the holding tank 74. Or, when the hydrogen peroxide level is above a maximum selected concentration, the sensor signals the electrolysis unit to switch off.

The system enables the concentration of peracetic acid to be selected within a wide range, of from about 0 to 35% peracetic acid. Concentrations of 10 to 3500 ppm are readily formed for sterilization and disinfection purposes. For example, catholyte solution with a hydrogen peroxide concentration of around 200–1000 ppm is readily obtained in under 5 minutes from the start of applying the potential. Adding a peracetic acid precursor to the catholyte in a proportional amount (i.e., in an approximately stoichiometric amount) has been found to generate solutions of peracetic acid at concentrations suitable for sterilization or disinfection. For example, adding about 5 g/L of acetyl salicylic acid solution to about a 400–700 ppm hydrogen peroxide solution yields a peracetic acid solution of about 1800 ppm. However, above a maximum hydrogen peroxide concentration, the peracetic acid concentration tends not to increase. For example, a hydrogen peroxide concentration of 1000 ppm did not appreciably increase the peracetic acid concentration as compared with a 200 ppm hydrogen peroxide concentration.

The resulting peracetic acid solution may be diluted, as desired, to an appropriate concentration for the application in which it is to be used. Optionally, less than a stoichiometric amount of the peracetic acid precursor is used so that the resulting antimicrobial solution contains both peracetic acid and hydrogen peroxide as antimicrobial agents. The peracetic acid concentration of this solution can be increased or revived by subsequent additions(s) of acetyl salicylic acid, or other acetyl donor.

In an alternative embodiment, the peracetic acid precursor, in either liquid or solid form, is mixed with the alkaline electrolyte, prior to electrolysis of oxygen, to form a solution of the alkaline electrolyte and the precursor. Specifically, the peracetic acid precursor is mixed with the alkaline electrolyte in the reservoir 50, or supplied directly to the chamber through a second inlet 88. Because some acetyl donors, in particular, acetyl salicylic acid, tend to hydrolyze at high pH (typically above about pH 12) it is preferable, in this embodiment, to buffer the alkaline electrolyte to a pH of about 11 or below, more preferably, about 9 or below, most preferably, around pH 7–8. Where the acetyl donor is combined with the alkaline electrolyte in the reservoir 50 and stored for a period of time, for example, it is desirable to buffer the combined solution within the reservoir to a pH of about 7–8. If the acetyl donor is supplied to the cathode chamber 14 separately from the alkaline electrolyte, the buffering agent may be added directly to the chamber 14 or supplied to the chamber mixed with the peracetic acid precursor. In this embodiment, the peracetic acid precursor is available to begin reacting with the peroxide species as soon as the peroxide is generated. However, the reaction between the peroxide and the precursor may continue to occur even after the catholyte has left the cathode chamber.

Other additives may be added to the catholyte solution, either before, during, or after generation of peracetic acid, to provide a suitable antimicrobial solution when combined with the peracetic acid and other oxidants present. These additives may include buffers, corrosion inhibitors, surfactants, sequestrants, chelating agents, and the like. They may be added in liquid or solid form.

Phosphates of alkali metals are suitable buffers for all of the embodiments described herein. One preferred buffering system includes a combination of monosodium phosphate, disodium phosphate, and tripolyphosphates. Such a buffering system also provides anticorrosion properties. Another preferred buffering system includes one or more potassium phosphates. Other suitable buffers include silicates, such as zeolites. The buffering system also serves to buffer the resulting peracetic acid solution to a suitable pH for effective antimicrobial decontamination, as will be described in further detail herein. A single buffering system can be used for buffering the alkaline electrolyte during peroxide formation and then subsequently used for buffering the antimicrobial solution.

Corrosion inhibiting and surface energy reducing additives are optionally introduced into the catholyte solution or to the resulting peracetic acid solution, either by adding them to the alkaline electrolyte prior to electrolysis, or during, or subsequent thereto. Other additives, including, but not limited to, detergents, chelators and sequestering agents, may also be added to the solution, either in combination with the other additives, or separately.

The corrosion inhibitory agents are selected in accordance with the nature of the materials in the items being cleaned and/or decontaminated with the oxidizing species. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

Copper and brass corrosion inhibitors include benzoates, azoles, such as triazoles, tolyltriazoles, dimercaptothiadiazoles, and other five-membered ring compounds. Particularly preferred copper and brass corrosion inhibitors include sodium salts of benzotriazole and tolyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and/or cleaned and also leaves deposits on parts of the electrolysis system. In such cases, a sequestering agent appropriate to prevent precipitation, such as sodium hexametaphosphate (HMP), or trisodium nitrilotriacetic acid (NTA Na$_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated. However, to ensure universal applicability with any water that might be utilized, the presence of a sequestering agent is preferred.

A surface energy reducing agent (surfactant)/wetting agent is optionally added to the peracetic acid solution to increase penetration into crevices of items being treated. This is particularly important when cleaning and decontaminating complex medical instruments, which may harbor microbial contaminants in crevices, joints, and lumens. Surfactants include anionic, cationic, nonionic, amphoteric, and/or zwitterionic surfactants. Specific classes which are useful include anionic and nonionic surfactants or combinations thereof. Examples of nonionic surfactants usable in the present invention include fatty alcohol polyglycol ethers, nonylphenoxypoly (ethyleneoxy) ethanol, and ethoxylated polyoxypropylene. Specific examples include Genapol UD-50™, Igepal™, Fluowet™, and Pegol™. The surfactants set forth above may be used alone or in combination with each other.

Amounts of corrosion inhibitors and surfactants to be added to the peracetic acid solution will vary depending upon the type of agent being added and whether or not one or more agents are added.

The inorganic corrosion inhibitors are preferably present in amounts ranging from about 0.01 to 20.0 weight per volume (w/v). Organic corrosion inhibitors are preferably present in amounts ranging from about 0.01% to 5.0% w/v. Phosphates are effective at concentrations in the range of about 0.01% to about 11.0% w/v.

The surfactants are preferably present in amounts ranging from about 0.0001% to about 5.0% w/v. More preferably, the surfactant is present in amounts ranging from about 0.0001% to about 0.5% w/v.

The electrolysis unit 10 thus described is suited to batch or continuous supply processes. Dilute solutions of the oxidizing species generated, such as peracetic acid, are advantageously used as antimicrobial solutions for sterilization or disinfection, although the peracetic acid, and or other oxidizing species generated, is optionally used for other purposes. In one preferred embodiment, the unit is used for generating batches of peracetic acid solution which can be used immediately, for disinfecting or sterilizing items, or stored for later use.

In another embodiment, the unit 10 is used to produce a stream of peracetic acid solution. The peracetic acid is carried from the holding tank 74, where present, or directly from the cathode chamber, via a fluid line 89 to a decontamination system 90 or other site at which items to be microbially decontaminated are immersed in, sprayed with, or otherwise contacted with the peracetic acid solution. The peracetic acid solution may also be supplied to a vaporizer where it is converted to vapor phase peracetic acid.

This embodiment is suited to a variety of purposes, such as decontamination of equipment, including food processing, medical, and pharmaceutical equipment, for disinfecting packaging such as food containers, for removing Listeria and other bacteria from processed food, such as hot dogs and other cooked and uncooked meats and meat products, including whole carcasses, and for sterilizing waste and water. Other applications for the peracetic acid and other oxidants generated include bleaching and as a raw material for a variety of chemical synthesis processes.

In one particular embodiment, processed foods, such as hot dogs, are sprayed with a solution containing the peracetic acid while being transported along a conveyor system.

Another embodiment includes the recirculation of a sterilant or disinfectant solution containing the peracetic acid generated. A return line 92 carries the used peracetic acid solution from a site 90 at which items are sterilized or disinfected, to the cathode chamber 14 of the electrolysis unit 10. The pump 52 or the pump 76 recirculates the decontaminant solution. Alternatively, the solution can be recirculated directly from reservoir 74 bypassing site 90 to maintain or enhance the concentration in the reservoir 74. The peracetic acid concentration of the solution is increased by generating further peroxide and/or adding additional peracetic acid precursor. Alternatively, the peracetic acid precursor is added initially in excess so that further peracetic acid can be generated without addition of more precursor. Then the refreshed solution is returned to the site 90. The solution is preferably recirculated in this way until the desired peracetic acid concentration is achieved. Once the desired concentration is achieved, the recirculation may be continued intermittently to maintain the desired peracetic acid concentration. Alternatively, the solution is recirculated continuously and the potential applied or the compressor 26 operated intermittently to maintain the concentration.

A sensor 94 optionally detects the peracetic acid concentration. FIG. 1 shows the sensor positioned in the return line 92 between the site 90 at which sterilization takes place and the electrolysis unit, although other suitable locations in the circulation path are also contemplated. The sensor signals the control system, which causes additional peracetic acid to be generated when the concentration is below a predetermined level. Other sensors for detecting hydrogen peroxide or other oxidizing species may also be employed. The sensors may be disposable or reusable. A variety of sensors may be used for detection of peracetic acid, including electrochemical sensors which use amperometric detection systems.

Figure 3:
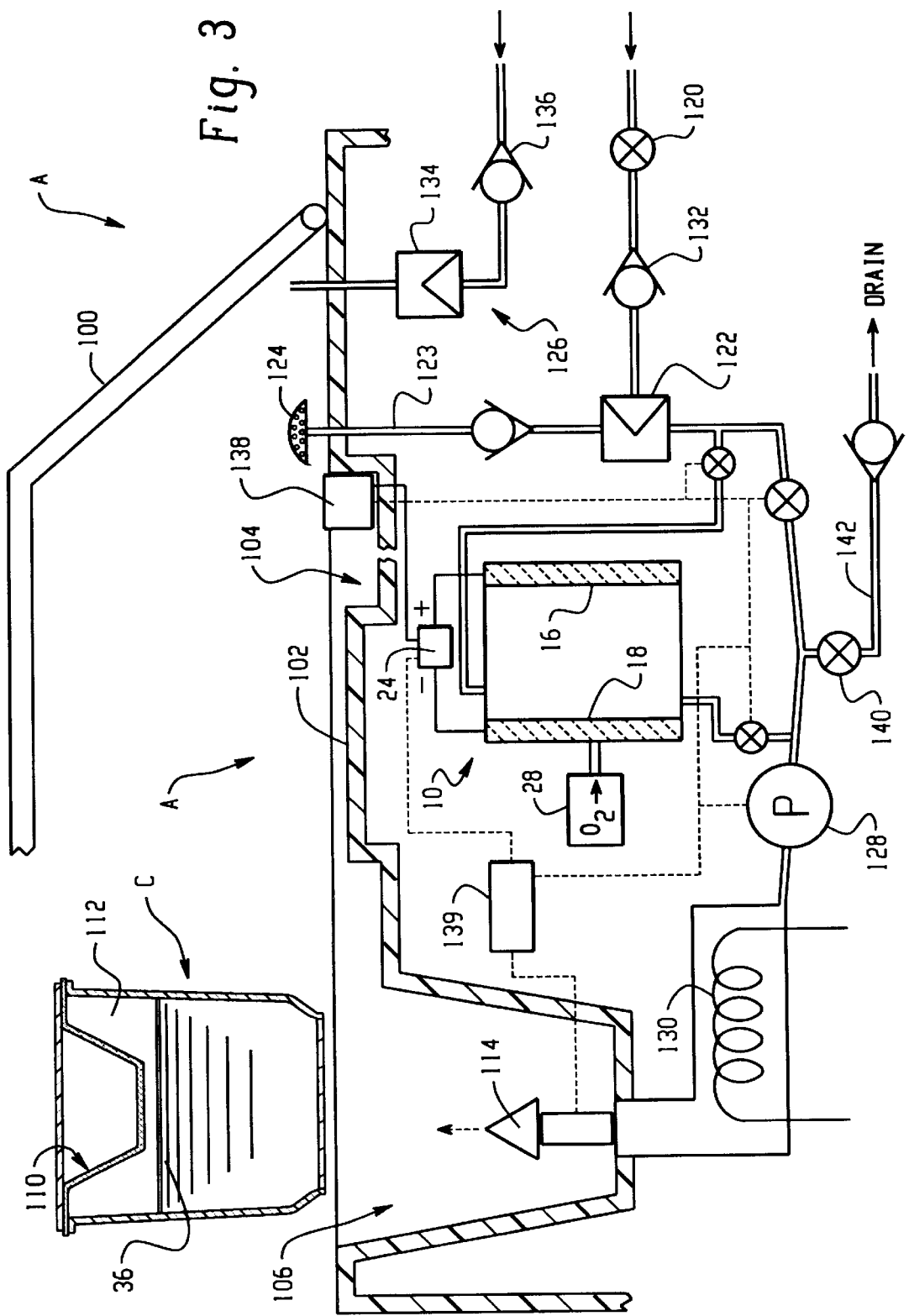
FIG. 3 is a plumbing diagram of a sterilization or disinfection system including the electrolysis unit of FIG. 1, a reagent cup receiving well, and a reagent cup.

With reference to FIG. 3, one embodiment of a system for recirculating a peracetic acid decontaminant solution through a decontamination system includes the electrolysis unit 10 and a microbial decontamination apparatus A, which is configured to sit on a counter top or other convenient work surface. While the system is described herein with particular reference to peracetic acid, it should be appreciated that the solution may also contain other oxidizing species which act as antimicrobial agents, such as hydrogen peroxide.

A door or lid 100 of the apparatus A is manually openable to provide access to a tray 102 which defines a receiving region 104 for receiving items to be microbially decontaminated, such as medical devices. In the illustrated embodiment, the tray 102 is configured to receive devices, such as endoscopes or other long, coilable items or to receive a cassette into which such items are preloaded. Other trays with item receiving regions of different configurations for receiving the items themselves or item-holding containers are also contemplated. A well 106 preferably receives a unit dose of reagents for forming a sterilant, disinfectant, or other microbial decontaminating solution. In one preferred embodiment, the dose of reagents includes a peracetic acid precursor, preferably in a solid form, such as acetyl salicylic acid, and a measured amount of concentrated alkaline electrolyte (salts, buffers, etc.) sufficient to provide the desired concentration on addition of water. Alternatively, the peracetic acid precursor, which may be liquid or solid, is added to the electrolysis unit from a vessel as described above, or introduced by other suitable means.

A reagent containing package C, which contains the dose of reagents, is inserted into the well 106. Optionally, the peracetic acid precursor is contained separately from the other reagents within the cup. In one preferred embodiment, the cup has a first compartment 110, which holds the peracetic acid precursor, and a second compartment 112, which holds the concentrated alkaline electrolyte. Other reagents, such as buffers, corrosion inhibitors, may be contained in one or other of the two compartments 110, 112, or separately added to the well, for example, in a third compartment.

In another embodiment, the peracetic acid precursor, buffers, and other additives are all contained in a single compartment cup C.

Once the items are loaded into the tray and the reagent carrying package C is inserted into the well, the lid 100 is closed and latched. A cup opener, such as a piston-operated cutter 114 is disposed at the bottom of the well 106. The cutter 114 cuts the base of the cup, or otherwise creates an opening in the cup, allowing the circulating water to dissolve or entrain the dose of reagents. Other dispensing systems are also contemplated.

In a preferred embodiment, the cutter 114 opens the compartment 112, containing the concentrated alkaline electrolyte, buffers, corrosion inhibitors, surfactants, and the like. These are circulated through the system to provide corrosion inhibition and buffer the circulating solution to the desired pH. The potential is applied across the cell 10 and generation of peroxide species begins. Then, the cutter 114 opens the compartment 110 containing the acetyl salicylic acid which circulates through the system and reacts with the peroxide species. The water and reagents are circulated through the electrolysis unit until a selected concentration of peracetic acid is reached.

Optionally, a fill valve 120 passes water through a microbe removing filter 122 in a fluid flow path 123 of a fluid circulating system. The microbe removing filter 122 blocks the passage of all particles of around $0.02\mu$ or larger. The incoming water, which has passed through the filter, is directed through a spray or distribution nozzle 124 and fills the item-receiving region 104 in the tray 102. As additional water is received, it flows into the well 106 dissolving solid reagents, or entraining liquid reagents, in the cup C, forming a solution. Filling is continued until all air is forced through an air system 126 and an entire interior volume is filled with the water. After the fill valve 120 is closed, a pump 128 circulates the fluid through the item receiving region 104 of the tray, the well 106, the electrolysis unit 10, and, optionally, a heater 130. The pump also forces the antimicrobial solution through the filter 122 to a check valve 132 decontaminating the filter. Further, the pump forces the anti-microbial solution through another microbe filter 134 in the air system 126 to a check valve 136. The circulation is continued until sterilization or disinfection is achieved.

In yet another embodiment, the cup C includes an additional compartment which holds a cleaning agent, such as a detergent concentrate. The cutter opens the detergent compartment and the detergent is mixed with water and is circulated through the system to clean the items prior to microbially decontaminating them. The detergent solution is preferably drained from the electrolysis unit and tray, and the items rinsed with a rinse fluid, such as water, prior to addition of the peracetic acid forming components, buffers, surfactants, corrosion inhibitors, and the like.

A peracetic acid concentration sensor 138 optionally senses the concentration of peracetic acid in the decontamination apparatus A. In a preferred embodiment, the concentration sensor signals a control system 139 which controls the application of the potential across the anode 16 and cathode 18 or switches the potential off for a period of time while the peracetic acid remains above a minimum preselected concentration. When the peracetic acid concentration drops to the minimum preselected concentration, or below, the voltage is applied to bring the peracetic acid concentration up to the desired level. In an alternate embodiment, the concentration sensor controls the valves which direct flow, through and around the electrolysis unit 10 to control concentration in the decontamination apparatus.

Alternatively or additionally, the control system 139 controls the further addition of the peracetic acid precursor.

In yet another embodiment, a sensor (not shown) detects hydrogen peroxide.

When decontamination is complete, a drain valve 140 in a drain line 142 is opened, allowing the solution to drain from the system. Optionally, the drain line is fluidly connected to the electrolysis unit for carrying the used peracetic acid solution back to the unit for destruction of oxidizing species. Air is drawn through the microbe filter 134 such that sterile air replaces the fluid within the system. Thereafter, the drain valve is closed and the fill valve 120 is opened again to fill the system with a sterile rinse fluid.

Figure 4:
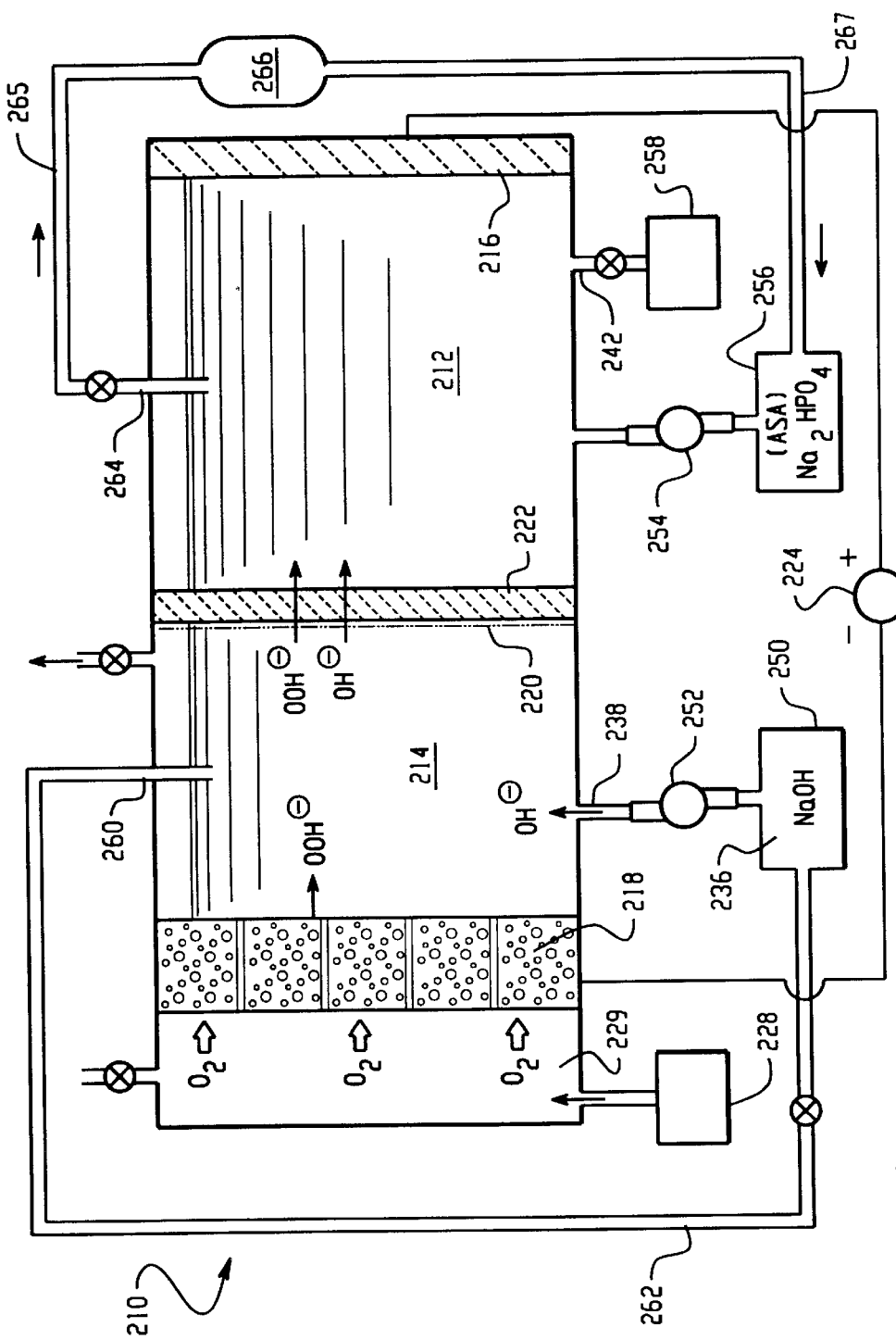
FIG. 4 is second alternative embodiment of an electrolysis unit according to the present invention.

With reference now to FIG. 4, another embodiment of an electrolysis unit 210 is shown. The unit is similar to that of FIG. 1, in that it includes two electrode chambers, namely an anodic chamber 212 and a cathodic chamber 214. An anode 216 forms a wall of the anodic chamber and a gas diffusion cathode 218 forms a wall of the cathodic chamber. A barrier or membrane 220 connects the anodic and cathodic chambers 212, 214 and controls the flow of dissolved species between them. In this embodiment, however, the membrane is an anion exchange membrane, rather than a proton permeable membrane. The membrane permits the migration of anions, including $OH^-$ and $HO_2^-$, between the chambers 212, 214, but limits mixing of other species, such as cations, between the two chambers. Suitable anion exchange membranes include ammonium ion membranes obtainable from Tokayama Neosepta, Asahi Glass, Morgane, Pall, Sybron, Electrosynthesis Co., and others, such as AMH and Asahi Glass Model AMP, both obtainable from Electrosynthesis Co. Optionally, the membrane is supported on a liquid permeable support wall 222, such as a porous ceramic.

A source of electric potential 224 applies a potential across the anode 216 and cathode 218. A compressor 228 supplies air or pure oxygen to the gas diffusion electrode 218. The air enters the gas diffusion cathode 218 where it reacts with an alkaline electrolyte at the liquid-gas-solid interface within the cathode. As in the case of the electrolysis unit of FIG. 1, the applied potential causes the generation of peroxide ions ($HO_2^-$) at the cathode 218 in an alkaline electrolyte 236. In this embodiment, the alkaline electrolyte includes an alkali, such as sodium or potassium hydroxide, which is supplied to the cathode chamber through an inlet 238. A 0.1M to about 1M sodium hydroxide solution at a pH of 12–14 is preferably used, although more dilute solutions may also be used. The alkaline electrolyte is thus highly basic and is maintained at pH about 12–14 by the incoming alkali.

An acidic electrolyte 240 (not shown) is fed to the anode chamber through an inlet 242. In this embodiment, the acidic electrolyte preferably contains a buffering system, such as described for the embodiment of FIG. 1, which buffers the pH of the acid electrolyte to a pH of around 5–9, more preferably, to a pH of about 7–8. (As noted earlier, the acid electrolyte may have a pH above 7, provided it is more acidic than the alkaline electrolyte.) An acid, such as sulphuric acid, may also be added to the acid electrolyte to adjust the pH, if desired. As with the embodiment of FIG. 1, the pH gradient between the cathode and anode chambers is preferably about 4–9, more preferably, about 5–7.

The sodium hydroxide solution (alkaline electrolyte) is delivered to the cathodic chamber inlet 238 from a reservoir 250 by a pump 252, or other convenient delivery system. A second pump 254 pumps the acid electrolyte to the anode chamber inlet 242 from a reservoir 256.

Suitable temperatures, electric charge, and other operating conditions for the electrolysis unit of FIG. 4 are as for the embodiment of FIG. 1, where not expressly stated otherwise.

The peroxide ions formed by reduction of oxygen at the cathode migrate through the anion exchange membrane 220 to the anode chamber 212. In the embodiment of FIG. 4, a peracetic acid precursor is supplied to the anode chamber 212 (rather than to the cathode chamber as in the embodiment of FIG. 1) where it reacts with the peroxide ions which have passed through the membrane 220. The peracetic acid precursor may be any of those previously listed and may be added directly to the anode chamber 212 from a precursor reservoir 258 or mixed with the acid electrolyte in the reservoir 256.

In this embodiment, it is the sodium hydroxide (alkaline electrolyte), which is essentially unconsumed in the electrolysis process. It is withdrawn from the anode chamber 212, through a return line 260 by pump 252 and returned to the chamber 214. In this way, a constant flow of the alkaline electrolyte over the cathode is maintained. Or, the alkaline electrolyte may be stirred in the chamber 214. The antimicrobial solution containing the peracetic acid formed in the anode chamber is withdrawn from the anode chamber through an outlet 264 and carried by a fluid line 265 to a site 266 at which items are to be decontaminated, such as the unit A. The decontaminant solution may be recirculated through the anode chamber one or more times to increase the peracetic acid concentration. Further additions of the acetyl donor to the recirculating solution may be made from the reservoir 258, as desired.

As for the embodiment of FIG. 1, additives, such as buffers, corrosion inhibitors, surfactants, and the like, may be added, but in this embodiment they are added to the acid electrolyte, either directly to the anodic chamber 212, or to the peracetic acid solution after leaving the chamber. The additives may be added either prior to, during, or after generation of peracetic acid, in either liquid or solid form. In a preferred embodiment, the buffers are added to the reservoir 256 and buffer the acid electrolyte to a pH of about 5–9, more preferably, to a pH of about 7–8. In another embodiment, the buffers, etc., are added directly to the chamber, or mixed with the peracetic acid precursor in reservoir 258.

As will readily be appreciated, the electrolysis unit 210 may be employed in a similar decontamination system to that shown in FIG. 3, although in this case, the solution circulating through the fluid flow paths, the tray 102, and the well 106, passes through the anode chamber 212 of the electrolysis unit 210, rather than the cathode chamber 214. A multi-compartment cup C may also be used in this embodiment, with the first compartment 112 holding a peracetic acid precursor and the second compartment 110 holding the acidic electrolyte. Buffers, corrosion inhibitors, surfactants, sequestering agents, and other additives are disposed in one or other of the compartments 110, 112 or separately added to the well 106.

Figure 5:
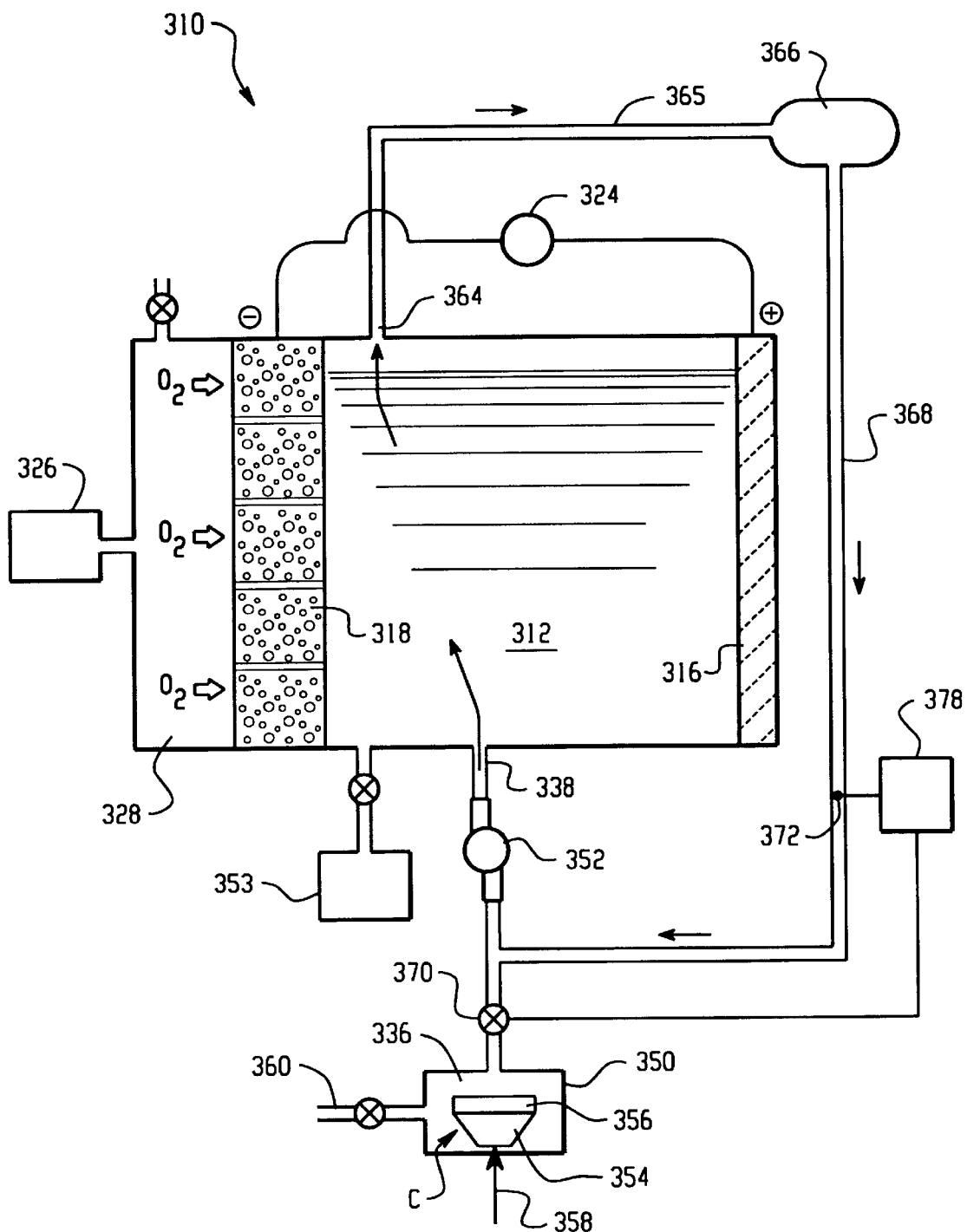
FIG. 5 is a third alternative embodiment of an electrolysis unit according to the present invention.

With reference now to FIG. 5, another embodiment of an electrolysis unit 310 is shown. The unit includes a single chamber 312. An anode 316 forms a first wall of the chamber and a gas diffusion cathode 318 forms a second wall of the chamber. Suitable anodes and cathodes are as previously described. As will be appreciated, no membrane is needed in this embodiment as only one electrolyte chamber 312 is employed.

A source of electric potential 324 applies a potential across the anode 316 and cathode 318. A compressor 326 supplies air or pure oxygen to the gas diffusion electrode 318. The air enters the electrode and is reduced at the air:liquid:solid interface. As in the case of the electrolysis unit of FIG. 1, the applied potential causes the generation of peroxide ions ($HO_2^-$) at the cathode 318 in an electrolyte 336. The peroxide and hydrogen peroxide formed react with a peracetic acid precursor to form peracetic acid. The peracetic acid precursor is preferably one of those previously listed.

In this embodiment, the electrolyte includes a charge carrying species, such as a phosphate, carbonate, or silicate, which may also act as a buffer. Acids or bases may also be added to adjust the pH. A peracetic acid precursor, preferably selected from those previously listed, such as acetyl salicylic acid, is added to the electrolyte prior to, during, or after hydrogen peroxide generation.

The electrolyte containing the acetyl salicylic acid, or other peracetic acid precursor, preferably has a pH of between about 2 and about 14, more preferably from about 5–9, and most preferably about 7–8. At high pH, generation of peracetic acid occurs rapidly, but the peracetic acid tends to break down fairly rapidly also. Additionally, where acetyl salicylic acid is the peracetic acid precursor, it tends to decompose rapidly at a pH over about 12, rendering it ineffective as an acetyl donor. At low pH, peracetic acid generation is much slower, but decomposition of peracetic acid is also slower. Thus, the preferred pH is partly dependent on the desired rate of peracetic acid generation, and also on the desired lifetime of the peracetic acid generated, and on the deterioration time for the acetyl donor at the selected pH. For some applications, it may be desirable to generate the peracetic acid quickly and then buffer the resultant solution with a buffer, once outside the electrolysis unit.

The electrolyte is supplied to the chamber through an inlet 338 from a reservoir 350 by a pump 352, or other convenient means. Suitable temperatures, electric charge, and other operating conditions for the electrolysis unit of FIG. 5 are as for the embodiment of FIG. 1, where not expressly stated otherwise.

The peroxide ions formed by reduction of oxygen at the cathode 318 react with the peracetic acid precursor. The peracetic acid precursor may be added directly to the anode chamber from a separate precursor reservoir 353 or mixed with the electrolyte in the reservoir 350.

In a preferred embodiment, a two compartment cup C holds buffers, and other additives, such as corrosion inhibitors, sequestrants, and surfactants in a first compartment 354 and a peracetic acid precursor, such as acetyl salicylic acid, in a second compartment 356. (As discussed for the embodiment of FIG. 3, a cleaning step may also be used in the embodiments of FIGS. 4 and 5 by adding an additional compartment to the cup C, which holds a concentrated cleaner.) A cup cutter 358, or other suitable cup-opening member, sequentially opens the first and second compartments, releasing the buffers and other additives, then the peracetic acid precursor, into the reservoir. A supply of water delivers fresh water to the reservoir through a water inlet line 360. The water mixes with the peracetic acid precursor and other additives to form a solution which is pumped by the pump 352 to the chamber 312. Alternatively, corrosion inhibitors, and other additives are added to the electrolyte after formation of peracetic acid.

The antimicrobial solution containing the peracetic acid formed in the chamber is withdrawn from the chamber through an outlet 364 and carried by a fluid line 365 to a site 366 at which items are to be decontaminated (such as the tray 102 of FIG. 3). The decontaminant solution may be recirculated through the chamber one or more times to increase the peracetic acid concentration. As shown in FIG. 5, a return fluid line 368 carries the used peracetic acid solution back to the chamber 312 from the site 366. Further additions of the acetyl donor to the recirculating solution may be made from the reservoir 350, by opening a valve 370 in the inlet line between the reservoir and the chamber 312, as desired. Alternatively, additional precursor may be added from the separate reservoir 353, such as by pumping a metered amount of an aqueous solution of the precursor from the separate reservoir to the chamber.

In another embodiment, at least a portion of the circulating peracetic acid is recirculated through the reservoir 350. This helps to ensure that all of the materials in the cup C are washed out of the reservoir 350 and carried to the chamber 312.

In yet another embodiment, the buffers, etc., are added directly to the chamber, or added to the peracetic acid in the supply line 365.

Peracetic acid concentration is measured by a sensor 372 placed in contact with the peracetic acid flowing through the fluid lines. The sensor signals a control system 378 which operates valve 370 to add more peracetic acid precursor from reservoir 350 (or from the separate reservoir 353), as needed, to bring the peracetic acid concentration up to a desired level.

As will readily be appreciated, the electrolysis unit 310 may be employed in a similar decontamination system to that shown in FIG. 3, although in this case, the solution circulating through the fluid flow paths, the tray 102, and the well 106, passes through the single chamber 312 of the electrolysis unit 310, rather than through an anode or a cathode chamber.

In several applications, it is desirable to maintain the peracetic acid at or slightly above a minimum level for extended periods. For example, in the spray treatment of food containers or food stuffs, such as precooked hotdogs, or in other treatment processes where a conveyor system is used to transport items to be sterilized through the antimicrobial spray, it is desirable for the sprayed antimicrobial solution to be recirculated and reused for extended periods, such as hours or even days. Even in relatively short term antimicrobial processes, which are effected in an hour or less, such as the sterilization of medical instruments, the presence of bodily fluids or other contaminants may degrade the peracetic acid such that it is desirable to replenish the peracetic acid concentration during the process. The peracetic acid solution can be maintained at the preselected level in a number of ways.

In one method, the acetyl salicylic acid, or other precursor, is added to the appropriate electrolyte (the alkaline electrolyte in the embodiment of FIG. 1, the acid electrolyte in the embodiment of FIG. 4, the single electrolyte in the embodiment of FIG. 5) in excess. Hydrogen peroxide is generated in a sufficient amount to react with a portion of the acetyl salicylic acid and bring the peracetic acid concentration up to the desired level. Then the potential (and/or the supply of oxygen) is switched off. When the peracetic acid becomes depleted, the potential is reapplied (or the supply of oxygen switched on) and more peroxide is generated. This combines with some of the residual acetyl salicylic acid to form peracetic acid.

In a second method, additional acetyl salicylic acid is added to the recirculating peracetic acid solution as needed. In this method, the potential may be applied to the electrolysis unit continuously or intermittently.

In a third method, decomposition products of peracetic acid (such as acetic acid) act as peracetic acid precursors which are reconverted to peracetic acid in the electrolysis unit by reaction with peroxide species.

In a fourth method, peracetic acid is generated at higher concentration than is need and diluted on its way to the site. The concentration can be maintained by further additions of the concentrated peracetic acid solution, as needed.

The peracetic acid solution may be stored in a vessel for later use (batch process), generated on demand to provide a continuous or intermittent flow of solution, or recirculated through the system to increase the peracetic acid concentration, either with or without passing the solution through a site at which items are to be decontaminated.

The peracetic acid generated has a wide variety of applications. Table 1 lists exemplary applications, and the preferred concentration of peracetic acid for these applications.

TABLE 1

APPLICATIONS FOR ELECTROCHEMICALLY
GENERATED PERACETIC ACID

| APPLICATION | PREFERRED PERACETIC ACID CONCENTRATION |
| --- | --- |
| Production of germ free animals | 1% of 1 ml |
| Food equipment decontamination | 50–1000 ppm |
| Beverage and brewing | 250–1000 ppm |
| Dairy industries | 120–300 ppm |
| Road tankers and animal transport containers | 150–500 ppm |
| Circuit water in cooling systems and processing plants | 10–400 ppm |
| Piping and membrane filters and water treatment for biofilm reduction | 21–340 ppm |
| Disinfect exchange resin columns for water supplies and chromatography | 1500 ppm |
| Sludge and effluent in municipal sewage plants | 5–500 ppm |
| Water treatment | 2–10 ppm |
| Treatment of processed food products | 500–4000 ppm |

While not intended to limit the invention, the following examples are illustrative of the methods of preparing the antimicrobial solutions containing one or more oxidizing agents.

EXAMPLES

Example 1
Generation of Peracetic Acid in the Cathodic Chamber

An alkaline electrolyte for the catholyte was prepared by dissolving 50 g/L $Na_2HPO_4$ and 5 g/L acetyl salicylic acid in 2 liters of deionized water. An acid electrolyte for the anolyte was prepared by diluting 100 mL of concentrated sulphuric acid in 2 liters of deionized water to form a 5% $H_2SO_4$ solution. An electrolysis unit of the type shown in FIG. 1 was used. The cathode was a gas diffusion electrode formed from gold coated with carbon. A DSA anode was used. The membrane was a NAFION 450 cation exchange membrane. Peristaltic pumps were used to pump the two electrolytes from reservoirs to the respective cathode and anode chambers at a flow rate of about 15 mL/min. A current of 5 amps (current density 100 mA/cm²) and voltage of about 10 volts was applied to the cell. A compressor supplied air to the cathode. The anolyte was recirculated through the reservoir and anode chamber. The catholyte was withdrawn continuously from the cathode chamber and collected in sample containers. The catholyte was analyzed with indicator strips at intervals over a period of 45 minutes.

Within 30 seconds, a peracetic acid(PAA) concentration of 10–20 ppm was obtained. After 10 minutes, the peracetic acid concentration was about 1500 ppm and the hydrogen peroxide concentration was about 1000 ppm. The concentrations of peracetic acid and hydrogen peroxide remained at these levels throughout the 45 minute test.

Example 2

Generation of Peracetic Acid in the Cathodic Chamber

The method of Example 1 was used with a variety of different membranes, anode materials, starting pHs, and so forth. The different conditions evaluated are listed in Table 2.

TABLE 2

ELECTROCHEMICAL GENERATION OF
PAA IN THE CATHODIC CHAMBER

EXPERIMENTS

| | | |
| --- | --- | --- |
| Electrolytes | 1) Catholyte | $CH_3COOK$, $CH_3COONa$, $Na_2HPO_4$ & ASA |
| | 2) Anolyte | 5% $H_2SO_4$ |
| Membrane | | NAFION ™ 450 (Cationic) |
| Current Density | | 100 mA/cm² |
| Voltage | | 10–30 V |
| Anode | | DSA (Eltech) |
| Cathode | | GDE:C on Au, C on Ni |
| Starting pH | | 4–13 |
| Temperature | | 20–63° C. |
| Fluid Conditions | | Flow ~17 ml/min (single pass) |
| Gas for GED | | Air, 99.9% oxygen |

The acetyl donors used in the examples were obtained from Aldrich Chemical, with the exception of TAED (Fluke Chemical).

Table 3 lists exemplary tests for which significant levels of peracetic acid were obtained and provides the peracetic acid levels generated (see Experiment 1). As shown in Table 3, which also lists experiments with an anion exchange membrane and no membrane, several of the acetyl donors were capable of providing peracetic acid in concentration suited to disinfection or sterilization. When a NAFION™ 450 cation exchange membrane was used, the peracetic acid was generated in the catholyte.

TABLE 3

ELECTROCHEMICAL GENERATION OF PAA BY CATHODIC SYNTHESIS
OF $H_2O_2$, EXEMPLARY TESTS AND PERACETIC ACID LEVELS GENERATED

| Experiment | Catholyte | Membrane | Anolyte | PAA Generated (PPM) |
| --- | --- | --- | --- | --- |
| 1. | $Na_2HPO_4$ + ASA (5 g/L) | NAFION ™ 450 | 5% $H_2SO_4$ | ~500 |
| 2. | NaOH | Neosepta | $Na_2HPO_4$ + ASA | 939 |
| 3. | $Na_2HPO_4$ + ASA (10 g/L) | None | Same as Catholyte | 737 |
| 4. | NaOH + ASA* (10 g/L) | None | Same as Catholyte | 2385 |
| 5. | NaOH + TAED* | None | Same as Catholyte | ~766 |

TABLE 3-continued

ELECTROCHEMICAL GENERATION OF PAA BY CATHODIC SYNTHESIS
OF $H_2O_2$, EXEMPLARY TESTS AND PERACETIC ACID LEVELS GENERATED

| Experiment | Catholyte | Membrane | Anolyte | PAA Generated (PPM) |
|---|---|---|---|---|
| 6. | NaOH + Citric Acid + Acetic Anhydride | None | Same as Catholyte | 101 |
| 7. | NaOH + α-D-Glucose pentaacetate* | None | Same as Catholyte | ~757 |
| 8. | NaOH + β-D-Glucose pentaacetate* | None | Same as Catholyte | ~562 |
| 9. | $Na_2HPO_4$ + citric acid + Sucrose octaacetate** | None | Same as catholyte | ~500 |

\* = 0–20 ml $CH_3COOH$ added to adjust pH
\*\* = 3 g/L citric acid added to adjust pH Peracetic acid was generated in all electrolytes where ASA was present, except those electrolytes with a pH of greater than 12. It is likely at high pH that the ASA was degraded to salicylic acid and acetic acid, rather than forming peracetic acid.

It was found that increasing the concentration of hydrogen peroxide did not significantly increase the peracetic acid concentrations. For example, the same level of peracetic acid was generated for hydrogen peroxide concentrations between 200 and 1000 ppm. No difference was found in peracetic acid concentration by using 99.9% oxygen as opposed to air. The temperature was found to have no effect on the peracetic acid generation, in the experimental range 20° to 63° C. A starting pH of between 5 and 11 was found to produce the best results. pHs above 11 caused ASA to hydrolyze rapidly.

Example 3
Generation of Peracetic Acid in the Anodic Chamber

Studies were made of the generation of peracetic acid in the anode chamber using an electrolysis unit similar to that shown in FIG. 3. The conditions used were the same as shown in Table 2, except that an anionic membrane (Tokuyama Neosepta) was used in all experiments, the catholyte was strongly basic, e.g., sodium hydroxide, and the acetyl donor and buffers were added to the anolyte, rather than to the catholyte. Since an anion exchange membrane was used, the peracetic acid was generated in the anolyte solution.

Table 3, Experiment 3, demonstrates the generation of peracetic acid at a concentration of 939 ppm when ASA was used as the acetyl donor.

Example 4
Generation of Peracetic Acid in a Single-Chamber Cell

An electrolyte was prepared by dissolving 50 g/L $Na_2HPO_4$ and 5 g/L acetyl salicylic acid in 2 liters of deionized water to form a solution having a pH of 7.7. An electrolysis unit of the type shown in FIG. 5 was used (a 50 $cm^2$ electrolyzer obtained from Eltech). The same unit was also used for EXAMPLES 5–7. The cathode was a gas diffusion electrode formed from gold coated with carbon. A DSA anode was used. A peristaltic pump was used to pump the electrolyte from the reservoir to the chamber at a flow rate of about 17 mL/min. A current of 5 amps (current density 100 mA/$cm^2$) and voltage of about 10 volts was applied to the cell. A compressor supplied air to the cathode. The electrolyte leaving the chamber was analyzed for peracetic acid with indicator strips, at intervals.

Within 10 minutes, the peracetic acid concentration was between 1000 and 2000 ppm and the hydrogen peroxide concentration was between 1000 and 2500 ppm.

Example 5
Generation of Peracetic Acid in a Single-Chamber Cell

The procedures of Example 4 were used with a variety of different electrolyte solutions (see Experiments 4–10, Table 3). Peracetic acid was generated in significant quantities in the single electrolyte when using no membrane. The highest peracetic acid concentrations (1700–2385 ppm), were obtained using sodium hydroxide and acetyl salicylic acid (pH 5 to 11).

Example 6
Rate of Peracetic Acid Generation with Various Acetyl Donors

Figure 6:
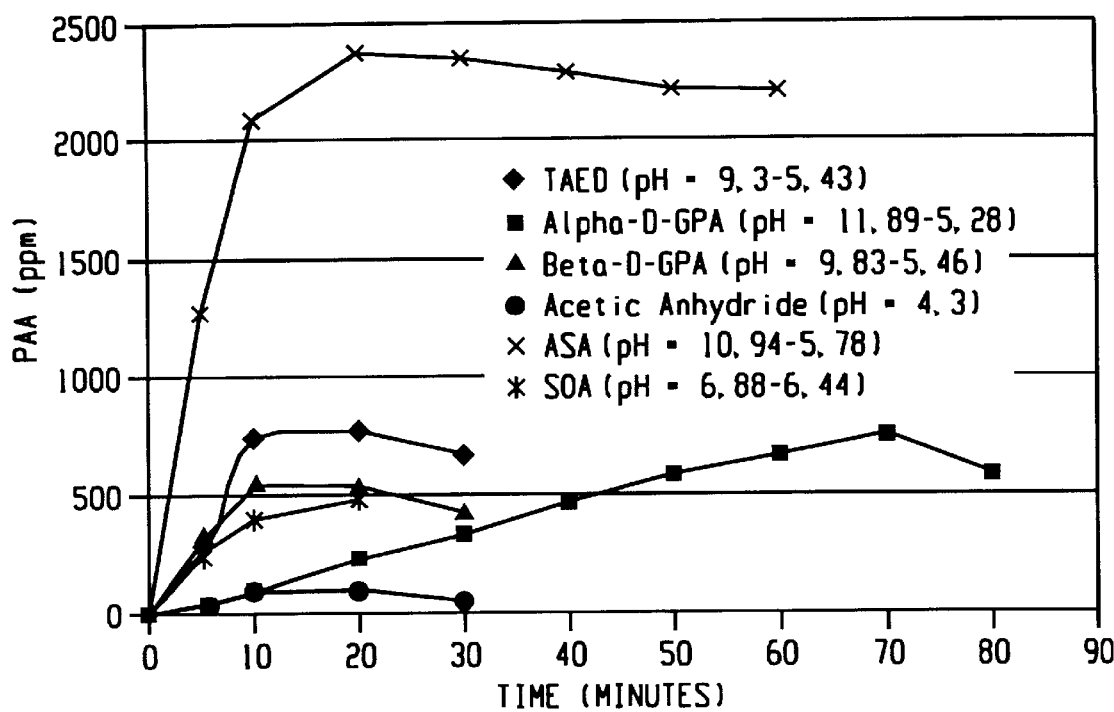
FIG. 6 is a plot of peracetic acid concentration versus time for five selected acetyl donors.

Time studies were carried out to determine the rate at which acetyl donors were capable of generating peracetic acid. A 50 $cm^2$ Eltech electrolyzer with no membrane or barrier was used for the tests with an electrolyte flow rate of about 17 mL/min and a current density of 100 mA/$cm^2$. A carbon on Ni mesh gas diffusion electrode was used as the cathode with an iridium oxide on titanium dimensionally stable anode. Both electrodes were obtained from Eltech corp. Table 4 shows the other experimental conditions used for six acetyl donors, TAED, α-D-Glucose pentaacetate (α-D-GPA), β-D-Glucose pentaacetate (β-D-GPA), acetic anhydride, sucrose octaacetate (SOA) and acetyl salicylic acid (ASA). FIG. 6 shows the generation of peracetic acid over time for each acetyl donor. Glacial acetic acid was used to adjust the pH for the following donors TAED, β-D-GPA, and ASA. Citric acid was used to adjust the pH of SOA. For α-D-GPA, a packet of the acetyl donor was contained within the cell.

TABLE 4

ELECTROCHEMICAL GENERATION OF PAA BY CATHODIC SYNTHESIS OF $H_2O_2$, CONDITIONS USED FOR SIX ACETYL DONORS

| Acetyl Donor | Electrolyte | pH adjuster | Maximum PAA Generated (PPM) | Voltage | Temp. |
|---|---|---|---|---|---|
| TAED (10 g/L) | NaOH (6 g/L) | glacial acetic acid (8mL/L) | 766 | 16.0–9.96 | 22.2–31.6 |
| α-D-GPA (4.3 g/L) | NaOH (6 g/L) | glacial acetic acid (8 ml/L) | 757 | 29.0–12.29 | 21.5–55.7 |
| β-D-GPA (10 g/L) | NaOH (6 g/L) | glacial acetic acid (8 mL/L) | 562 | 17.7–10.05 | 21.1–44.4 |
| acetic anhydride (25 mL/L) | NaOH (6 g/L) | citric acid (10 g/L) | 101 | 11.7–10.68 | 24.3–49.9 |
| ASA (10 g/L) | NaOH (6 g/L) | glacial acetic acid (9 mL/L) | 2385 | 18.5–10.14 | 20.8–46.7 |
| SOA (5 g/L) | $Na_2HPO_4$ | citric acid (3 g/L) | 498 | 12.95–10.20 | 40.8–60.7 |

TABLE 5

ELECTROCHEMICAL GENERATION OF PAA BY CATHODIC SYNTHESIS OF $H_2O_2$ WITH ASA AT DIFFERENT STARTING pHs

| Starting pH | pH adjuster | Maximum PAA Generated (PPM) | Voltage Range | Temp. Range (° C.) |
|---|---|---|---|---|
| 10.94 | acetic acid (4.5 mL/L) | 2385 | 18.5–10.14 | 20.8–46.7 |
| 10.87 | acetic acid (4.5 mL/L) | 2281 | 18.3–10.26 | 21.1–44.4 |
| 5.0 | acetic acid (8.3 mL/L) | 1792 | 17.8–10.6 | 21.8–43.1 |
| 6.78 | acetic acid (5 mL/L) | 1661 | 17.86–10.77 | 25.0–47.9 |
| 4.81 | acetic acid (8.35 mL/L) | 1796 | 20.0–11.13 | 20.8–44.4 |
| 4.8 | acetic acid (8.4 mL/L) | 1758 | 18.5–10.6 | 21.2–43.3 |
| 11.4 | acetic acid (3.75 mL/L) | 1259 | 21.70–10.88 | 22.1–42.6 |
| 11.14 | acetic acid (4.25 mL/L) | 945 | 20.5–10.91 | 21.2–43.7 |
| 11.9 | acetic acid (2.5 mL/L) | 759 | 18.6–10.56 | 22.5–44.7 |
| 12.44 | none | 84 | 13.36–9.30 | 21.1–45.8 |
| 12.4 | none | 0 | 12.2–9.6 | 22.9–37.7 |

As can be seen from FIG. 6, acetyl salicylic acid generated peracetic acid rapidly, reaching a peak after about 20 minutes. In contrast, the peracetic acid concentration continued to rise for about 70 minutes when α-D-GPA was used.

Example 7

Effect of pH on Rate of Peracetic Acid Generation by Acetyl Salicylic Acid

Figure 7:
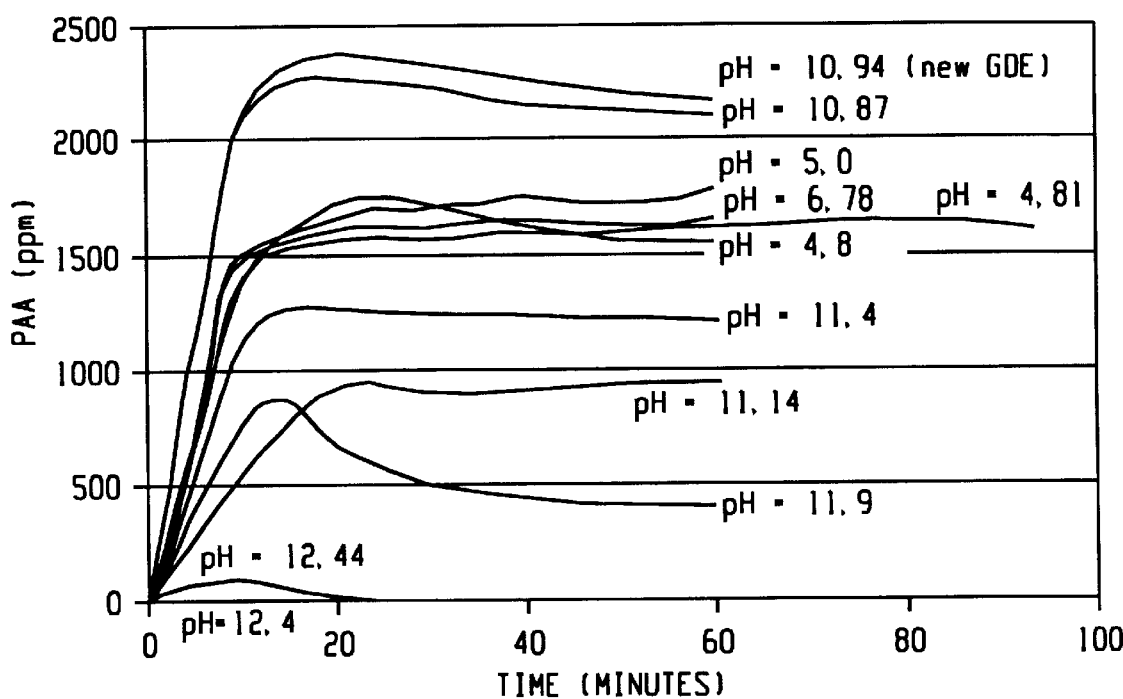
FIG. 7 is a plot of peracetic acid concentration versus time for various initial electrolyte starting pHs, using acetyl salicylic acid as an acetyl donor.

Experiments were carried out using different starting pHs to study the effect on peracetic acid generation with acetyl salicylic acid. A 50 cm² Eltech electrolyzer with no membrane or barrier was used for the tests with an electrolyte flow rate of about 17 mL/min and a current density of 100 mA/cm². A carbon on Ni mesh gas diffusion electrode was used as the cathode with an iridium oxide on titanium dimensionally stable anode. Both electrodes were obtained from Eltech Corp. In each case 10 g/L ASA was used as the acetyl donor in the electrolyte, which also included 6 g/L NaOH. Glacial acetic acid, in varying amounts was used to adjust the pH to the initial starting pH. TABLE 5 lists other experimental details for each experiment. FIG. 7 shows the effect of pH on peracetic acid concentration over time. For samples using high initial pH, the pH dropped over time. The lower pH electrolytes showed little or no drop in pH over time. For ASA, the highest levels of peracetic acid were generated in pH range of pH 10 to pH 11. However, above pH 11, the rapid hydrolyzation of ASA resulted in much lower peracetic acid concentrations.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for preparing an antimicrobial solution containing peracetic acid, the method comprising:
   electrolytically generating hydrogen peroxide or peroxide ions; and
   reacting the hydrogen peroxide or peroxide ions with an acetyl donor to form peracetic acid.

2. The method of claim 1, wherein the step of electrolytically generating hydrogen peroxide or peroxide ions is carried out at a cathode of an electrolysis unit, the electrolysis unit further including an anode.

3. The method of claim 2, wherein the step of electrolytically generating hydrogen peroxide or peroxide includes electrolysis of oxygenated water.

4. The method of claim 3, wherein the cathode is a gas diffusion electrode and the electrolysis of oxygenated water includes feeding an oxygen containing gas to the cathode, the cathode being in contact with an electrolyte which includes water.

5. The method of claim 4, wherein the electrolyte includes a charge carrying species.

6. The method of claim 5, wherein the charge carrying species is selected from the group consisting of acids, alkali and alkaline earth metal phosphates, carbonates, silicates, sulfates, and hydroxides, and combinations thereof.

7. The method of claim 3, wherein the cathode is separated from the anode by a membrane which separates the unit into an anode chamber and a cathode chamber, the membrane including one of a cation exchange membrane and an anion exchange membrane.

8. The method of claim 7, wherein the membrane is a cation exchange membrane, and the step of electrolytically generating hydrogen peroxide or peroxide ions includes:

generating hydrogen ions in an electrolyte in the anode chamber; and providing a pH differential across the membrane which drives the hydrogen ions to the cathode chamber.

9. The method of claim 8, wherein the pH differential is at least about 0.5.

10. The method of claim 8, wherein the step of reacting the hydrogen peroxide or peroxide ions with an acetyl donor includes:

introducing the acetyl donor to the cathode chamber.

11. The method of claim 7, wherein the membrane is an anion exchange membrane, the step of electrolytically generating hydrogen peroxide including:

generating hydrogen ions in an electrolyte in the anode chamber; and providing a pH differential across the membrane which drives peroxide ions to the anode chamber.

12. The method of claim 11, wherein the pH differential is at least about 0.5.

13. The method of claim 11, wherein the step of reacting the hydrogen peroxide or peroxide ions with an acetyl donor includes:

introducing the acetyl donor to the anode chamber.

14. The method of claim 4, wherein the oxygen containing gas is air.

15. The method of claim 1, wherein the acetyl donor is selected from the group consisting of acetyl salicylic acid, tetraacetyl ethylene diamine (TAED), acetic anhydride, cellulose acetates, and β-D-glucose pentaacetates, D-mannitol hexaacetate, sucrose octaacetate, and combination thereof.

16. The method of claim 15, wherein the acetyl donor includes acetyl salicylic acid.

17. A method of antimicrobial decontamination of items comprising:

a) supplying an oxygen containing gas to a cathode of an electrolysis unit;

b) reacting oxygen in the gas to form peroxide ions or hydrogen peroxide in an electrolyte at the cathode;

c) reacting the peroxide ions or hydrogen peroxide with an acetyl donor to form peracetic acid; and d) transporting the electrolyte containing peracetic acid to a site at which the items are microbially decontaminated.

18. A system for generating antimicrobial solution containing peracetic acid, the system comprising:

an electrolysis unit including:
an anode,
a cathode, and
a source of a potential which applies a potential between the anode and the cathode;

a source of an oxygen containing gas which supplies oxygen to the cathode for forming hydrogen peroxide or peroxide ions in an electrolyte; and a source of an acetyl donor, which supplies an acetyl donor for reacting with the hydrogen peroxide or peroxide ions to form a solution which includes peracetic acid.

19. The system of claim 18, further including:

a vessel for receiving items to be decontaminated;

a fluid supply line which carries the solution containing peracetic acid from the electrolysis unit to the vessel; and a storage reservoir connected with the supply line and the vessel, the storage reservoir storing solution containing peracetic acid.

20. The system of claim 18, further including:

a return line which re.urns electrolyte depleted of peracetic acid to the electrolysis unit for regeneration of peracetic acid.

21. The system of claim 18, wherein the electrolysis unit further includes:

a membrane which separates the anode from the cathode, the membrane being one of:
a cation permeable membrane, and
an anion permeable membrane.

22. The system of claim 18, further including:

a vessel for receiving items to be decontaminated; and a fluid supply line which carries the solution containing peracetic acid from the electrolysis unit to the vessel.

23. A method for preparing an antimicrobial solution containing peracetic acid, the method comprising:

supplying an oxygen containing gas to a cathode of an electrolysis unit;

reacting oxygen in the gas to form peroxide ions or hydrogen peroxide in an electrolyte at the cathode; and reacting the hydrogen peroxide or peroxide ions with an acetyl donor to form peracetic acid.

24. The method of claim 23, further including:

recirculating the electrolyte past the cathode to increase peracetic acid concentration.

25. The method of claim 23, further including:

adjusting the pH of the electrolyte to about 5–9.

26. The method of claim 23, further including:

adding at least one additive to the electrolyte, the additive being selected from the group consisting of surfactants, corrosion inhibitors, buffering agents, and chelating agents.

27. The method of claim 23, further including:

monitoring the electrolyte for at least one of:
hydrogen peroxide concentration;
peracetic acid concentration.

28. The method of claim 27, further including:

in response to the electrolyte being below a selected minimum hydrogen peroxide or peracetic acid concentration, controlling at least one of:
application of current to the electrolysis unit,
addition of peracetic acid precursor to the electrolyte, and
supply of oxygen containing gas to the cathode.

* * * * *

UNITED STATES PATENT AND TRADEMARK OFFICE
CERTIFICATE OF CORRECTION

PATENT NO. : 6,387,238 B1
DATED : May 14, 2002
INVENTOR(S) : Merk et al.

It is certified that error appears in the above-identified patent and that said Letters Patent is hereby corrected as shown below:

<u>Title page,</u>
Please correct the Related U.S. Application Data as follows:
Item -- [60] Provisional application No. 60/147,327, filed on Aug. 5, 1999. --

Signed and Sealed this

Twenty-fourth Day of September, 2002

Attest:

Attesting Officer

JAMES E. ROGAN
*Director of the United States Patent and Trademark Office*